United States Patent
Patel et al.

(10) Patent No.: US 10,660,739 B2
(45) Date of Patent: May 26, 2020

(54) KNOTLESS SUTURE OR TISSUE ANCHOR

(71) Applicant: Smith & Nephew, Inc., Memphis, TN (US)

(72) Inventors: Nehal N. Patel, Boston, MA (US); Matthew E. Koski, Westford, MA (US); Geoffrey I. Karasic, Milton, MA (US)

(73) Assignee: Smith & Nephew, Inc., Memphis, TN (US)

( * ) Notice: Subject to any disclaimer, the term of this patent is extended or adjusted under 35 U.S.C. 154(b) by 127 days.

(21) Appl. No.: 15/532,322

(22) PCT Filed: Dec. 22, 2015

(86) PCT No.: PCT/US2015/067479
§ 371 (c)(1),
(2) Date: Jun. 1, 2017

(87) PCT Pub. No.: WO2016/111856
PCT Pub. Date: Jul. 14, 2016

(65) Prior Publication Data
US 2017/0304044 A1    Oct. 26, 2017

Related U.S. Application Data

(60) Provisional application No. 62/100,108, filed on Jan. 6, 2015.

(51) Int. Cl.
*A61F 2/08*     (2006.01)
*A61B 17/04*    (2006.01)

(52) U.S. Cl.
CPC ........ *A61F 2/0811* (2013.01); *A61B 17/0401* (2013.01); *A61F 2/0805* (2013.01); *A61B 2017/044* (2013.01); *A61B 2017/0409* (2013.01); *A61B 2017/0412* (2013.01); *A61B 2017/0414* (2013.01); *A61B 2017/0445* (2013.01); *A61F 2002/0852* (2013.01); *A61F 2002/0888* (2013.01)

(58) Field of Classification Search
CPC .......... A61F 2/0811; A61F 2002/00817; A61F 2002/0829; A61B 17/0401
See application file for complete search history.

(56) References Cited

U.S. PATENT DOCUMENTS

2001/0041916 A1   11/2001   Bonutti
2002/0013608 A1    1/2002   ElAttrache et al.
(Continued)

FOREIGN PATENT DOCUMENTS

| EP | 2599449 | 6/2013 |
|---|---|---|
| FR | 2846867 | 11/2002 |
| WO | 2015134872 | 9/2015 |

*Primary Examiner* — Katherine M Rodjom
(74) *Attorney, Agent, or Firm* — Norman F. Hainer, Jr.

(57) ABSTRACT

Embodiments of the invention include methods and devices for securing a suture, graft, or other material to tissue with an anchor. The anchor of some embodiments includes an eyelet through which the suture, graft, or other material may be passed and mechanisms for selectively engaging the suture, graft, or other material through the eyelet. The mechanisms of some embodiments may also reinforce the anchor to provide a strengthened anchor to withstand actions such as impacting the anchor during insertion or applying bending stress to the anchor.

19 Claims, 5 Drawing Sheets

(56) References Cited

U.S. PATENT DOCUMENTS

| | | |
|---|---|---|
| 2005/0075668 A1 | 4/2005 | Lizardi |
| 2008/0051836 A1 | 2/2008 | Foerster et al. |
| 2009/0112270 A1* | 4/2009 | Lunn .................. A61B 17/0401 606/301 |
| 2009/0248068 A1 | 10/2009 | Lombardo et al. |
| 2009/0312794 A1 | 12/2009 | Nason et al. |
| 2010/0004683 A1* | 1/2010 | Hoof .................. A61B 17/0401 606/232 |
| 2010/0292731 A1 | 11/2010 | Gittings et al. |
| 2011/0004242 A1 | 1/2011 | Stchur |
| 2011/0112576 A1* | 5/2011 | Nguyen ............. A61B 17/0401 606/232 |
| 2013/0085529 A1 | 4/2013 | Housman |
| 2013/0103083 A1 | 4/2013 | Baird |
| 2013/0144334 A1 | 6/2013 | Bouduban et al. |
| 2013/0267998 A1 | 10/2013 | Vijay et al. |
| 2014/0222072 A1 | 8/2014 | Gerber et al. |
| 2014/0364906 A1* | 12/2014 | Palese ................ A61B 17/0401 606/232 |

* cited by examiner

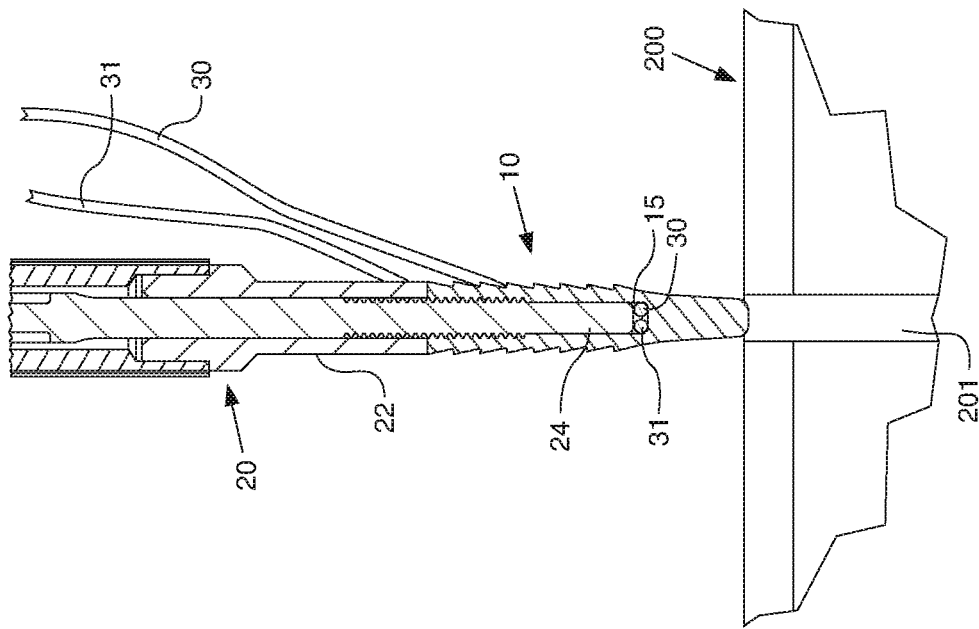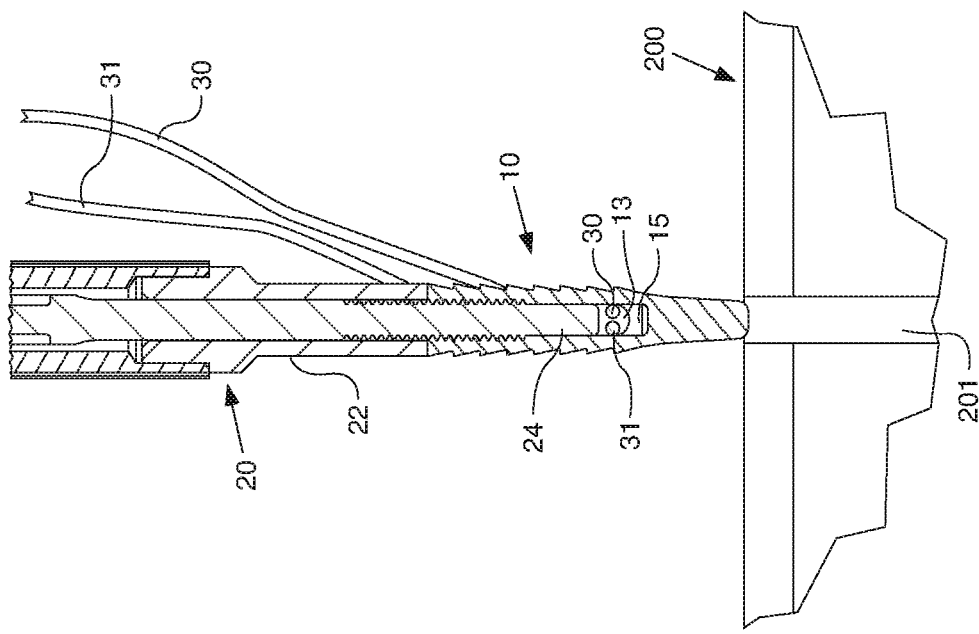

KNOTLESS SUTURE OR TISSUE ANCHOR

CROSS-REFERENCE TO RELATED APPLICATIONS

This application claims priority of U.S. application Ser. No. 62/100,108, filed Jan. 6, 2015, the disclosure of which is incorporated by reference in its entirety.

FIELD OF THE INVENTION

The present invention relates generally to the field of tissue anchors, and more particularly relates to knotless suture anchors or tissue anchors along with their implantation instruments and related methods. Some embodiments include an anchor and an implantation instrument with a portion of the instrument that both strengthens the anchor during implantation and selectively impinges on a suture or tissue graft to be attached with the anchor.

BACKGROUND

Anchors used to secure sutures, tissue grafts, or other components are ideally as small as possible while providing sufficient strength for their designed task. Smaller size may be advantageous to one or both decrease surgical trauma and to enable implantation in smaller anatomical structures. In some circumstances, such as but not limited to when an anchor is used in a knotless anchoring system where no guide instrument is provided, high stresses may be created in an anchor during implantation. Impacting, positioning, or repositioning of anchors may also create high stresses in an anchor. A specific non-limiting example of creating relatively high stresses in an anchor is when the anchor is used as a pivot point to lever a humeral head to gain an effective trajectory for implantation. In such a circumstance, an anchor that would be strong enough to meet load requirements of the anchor in a completed construct may not be of adequate strength to withstand the loads generated when being used as a pivot point. One way of addressing the need for a stronger anchor during implantation is to just use a larger diameter anchor. However, use of a larger diameter anchor may create additional surgical trauma and may not fit a patient's available anatomic implantation site in some circumstances.

It would be advantageous to provide an anchor that is of a relatively small size that may be strengthened or reinforced during implantation. Particular instrumentation and methods may also be required to implant such an anchor. It may be further advantageous to provide a portion of an implantation instrument that is capable of both strengthening or reinforcing an anchor and selectively engaging and disengaging suture or tissue that the anchor is used to attach.

SUMMARY

An embodiment of the invention is an anchor system that includes an anchor with an opening through its proximal end and an eyelet through the anchor that is transverse with and intersects the opening. The anchor system may also include an inserter that includes an outer shaft configured to contact the anchor and to be used to push the anchor into tissue, and a rod configured to fit within the outer shaft and move within the outer shaft and to move within the anchor when the outer shaft is in position to push the anchor into tissue. The rod may be configured to go through the opening in the proximal end of the anchor and to occlude the eyelet when advanced distally within the anchor. The rod may also support and improve the strength of the anchor system when advanced distally within the anchor.

Another embodiment of the invention is a method of anchoring to tissue. The method may include providing an anchor with an opening through its proximal end and an eyelet through the anchor that is transverse with and intersects the opening, and providing an inserter that includes a rod configured to fit within the anchor. The method may also include passing a suture through the eyelet, advancing the rod distally through the opening in the anchor far enough to occlude the eyelet, pushing the anchor into tissue at least as far as the proximal end of the anchor after the rod has been advanced distally through the opening in the anchor far enough to occlude the eyelet, and removing the rod proximally through the opening in the anchor.

Still another embodiment of the invention is a method of securing a suture to a bone that includes passing a suture through an eyelet in an anchor and engaging an inserter with the anchor and the suture to positively hold the suture relative to the anchor. The method embodiment may also include pushing the anchor into the bone with the inserter such that the suture is wedged between the anchor and the bone, thereby substantially preventing movement of the suture relative to the anchor, and removing the inserter from the anchor, leaving the anchor and the suture secured in the bone.

Yet another embodiment of the invention is a method of securing a suture to a bone that includes coupling the suture to an anchor system. The anchor system may include an anchor with an opening through its proximal end and an eyelet through the anchor that is transverse with and intersects the opening, and an inserter comprising an outer shaft configured to contact the anchor and to be used to push the anchor into tissue, and a rod housed within the outer shaft and the anchor, the rod extending through the opening in the proximal end of the anchor and configured to occlude the eyelet when advanced distally within the anchor. The method embodiment may further include pushing the anchor into the bone with the inserter such that the suture is wedged between the anchor and the bone, thereby substantially preventing movement of the suture relative to the anchor, and removing the inserter from the anchor, leaving the anchor and the suture secured in the bone.

BRIEF DESCRIPTION OF THE DRAWINGS

FIG. 6A is a cross-sectional view of the anchor, sutures, and distal end of the inserter of FIG. 1 being prepared to be implanted in tissue by advancing a portion of the inserter distally within the anchor.

FIG. 6B is a cross-sectional view of the anchor, sutures, and distal end of the inserter of FIG. 1 being prepared further to be implanted in tissue by advancing a portion of the inserter further distally within the anchor.

DETAILED DESCRIPTION

Figure 1:
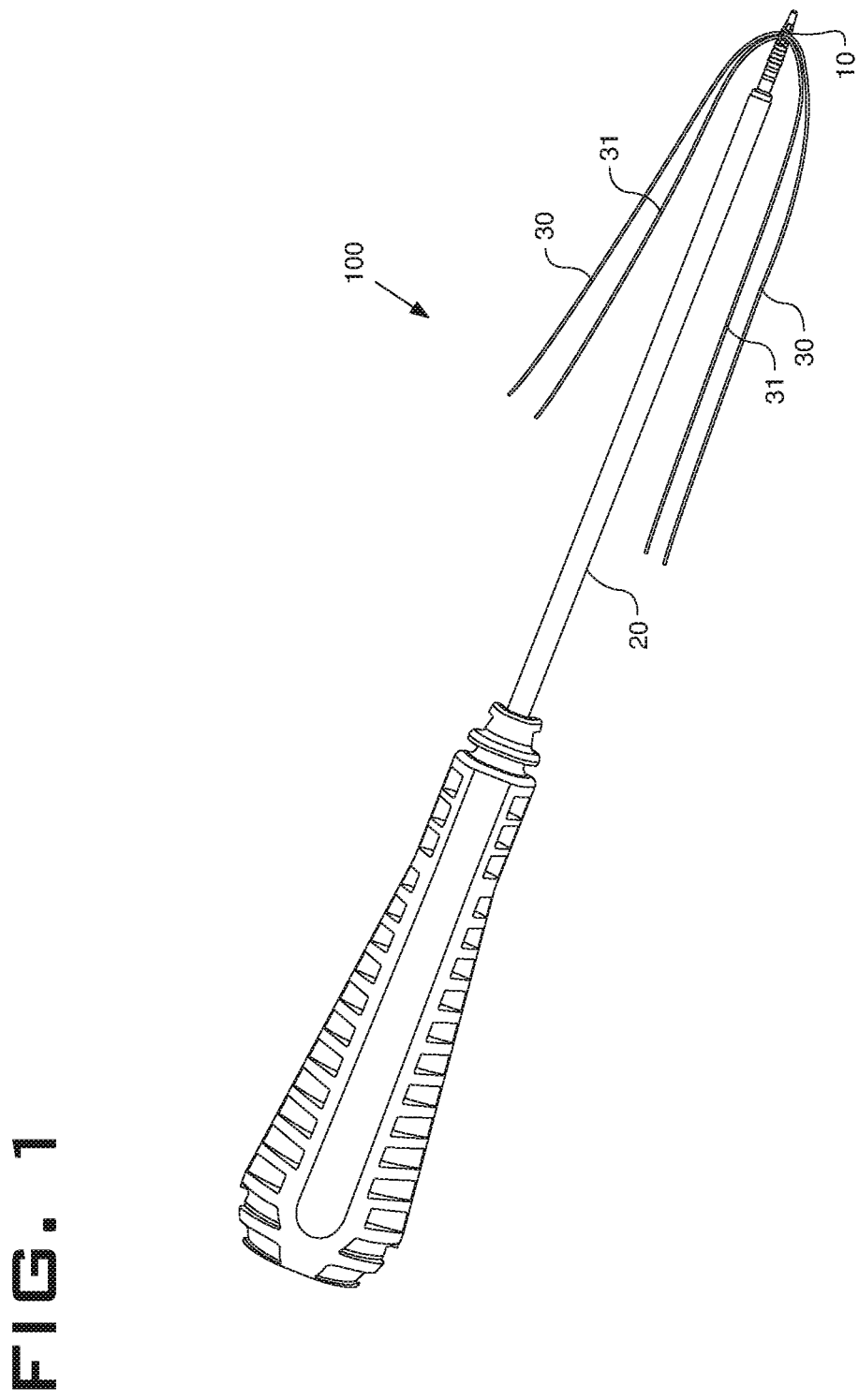
FIG. 1 is a perspective view of an anchor through which sutures have been passed where the anchor is coupled to an inserter.

An embodiment of an anchor system 100 and its component parts and methods of implementation are illustrated in FIGS. 1-6C. As depicted in FIG. 1, the anchor system 100 includes an anchor 10, an inserter 20, and sutures 30, 31. An embodiment of the anchor 10 is shown in FIGS. 1-6C. As most clearly seen in FIG. 4, the anchor 10 includes an opening 11 through its proximal end 12 and an eyelet 13 through the anchor 10 that is transverse with and intersects the opening 11. The opening 11 shown is cylindrical and includes a thread 17 around a proximal, interior portion of the opening 11. Openings of other embodiments may be of any other effective shape, and in addition to or instead of threads may include any other effective coupling mechanism, such as without limitation, a ball and detent, a clamp, or a snap ring. The opening 11 depicted is a partial cannulation that does not exit a distal end of the anchor. In other embodiments, an opening could include a full cannulation of the anchor or a cannulation that varies in shape or length from the shape and length of the opening 11. The anchor 10 shown includes protrusions 16 positioned around the exterior of the anchor 10 that are configured to create resistance to pull-out of the anchor 10 from tissue. As used herein, the term "tissue" may include any portion of the human body, including but not limited to bones, tendons, ligaments, cartilage, and periosteal components. The protrusions 16 shown are of a raked tooth shape. However, any effective shape may be used in other embodiments. For example and without limitation, protrusions may be triangular, square, pyramid shaped, shark's tooth shaped, and raked to a greater or lesser degree. The anchor 10 shown includes a basin 15. The basin 15 illustrated extends distally beyond a most distal portion of the eyelet 13.

Figure 5:
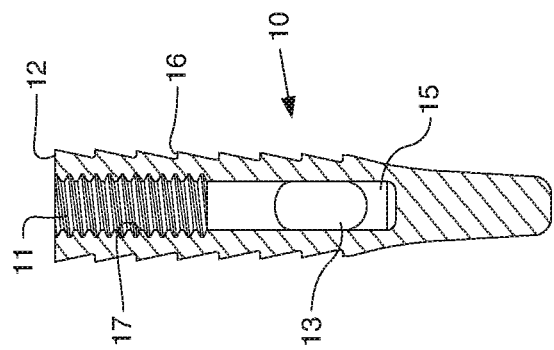
FIG. 5 is a cross-sectional view of the anchor and distal end of the inserter of FIG. 1.

As shown in FIG. 5, the basin 15 is configured to receive a rod 24 that is part of the inserter 20. The rod 24 may pinch the suture 30, 31 relative to the anchor 10 within the basin 15. The rod 24 may also, or in the alternative reinforce, strengthen, and support the anchor 10 by providing support for the anchor 10 within the opening 11, within the basin 15, and throughout the partial cannulation of the anchor 10. In the position shown in FIG. 5 where the rod 24 is advanced distally within the anchor 10 beyond a most distal portion of the eyelet 13 within the basin 15, the rod 24 supports and improves the bending strength of the anchor 10. Embodiments of a rod of the anchor system may be more generally described as supporting and improving the strength of the anchor system, whether in bending or otherwise, when the rod is position within or advanced distally within the anchor.

Figure 2:
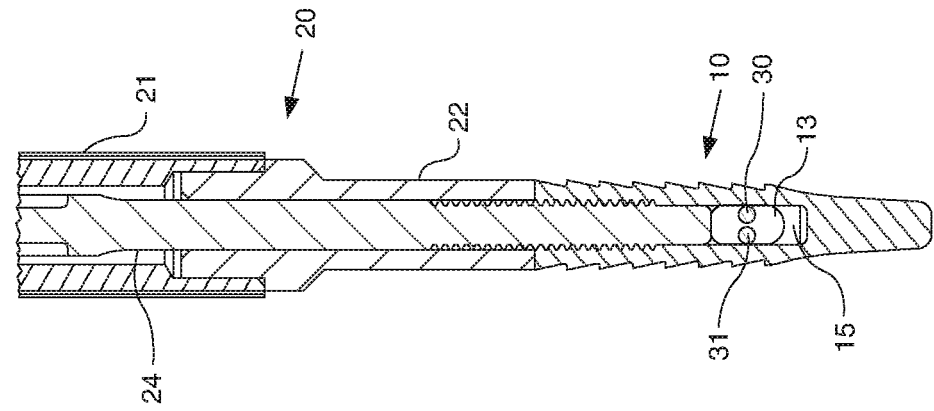
FIG. 2 is a side elevation view of the anchor and sutures of FIG. 1 and a distal end of the inserter of FIG. 1.
Figure 3:
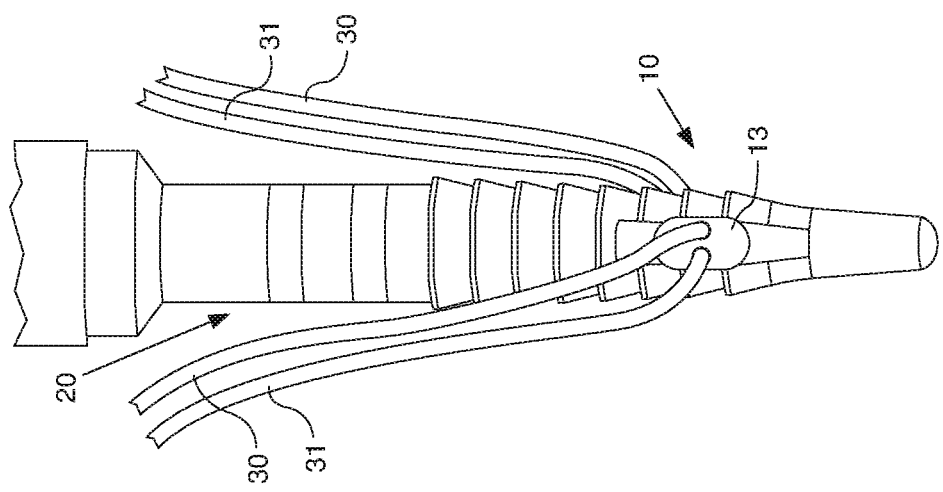
FIG. 3 is a cross-sectional view of the anchor, sutures, and distal end of the inserter of FIG. 1 with components in the relative positions illustrated in FIG. 2.
Figure 4:
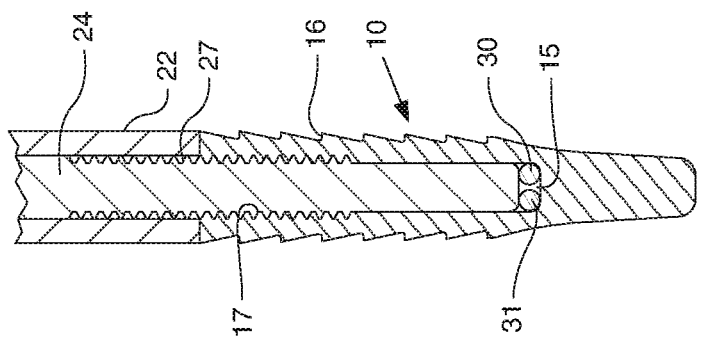
FIG. 4 is a cross-sectional view of the anchor of FIG. 1.

The inserter 20 includes an outer shaft 22 configured to contact the anchor 10 and to be used to push the anchor 10 into tissue. The contact between the outer shaft 22 and the anchor 10 may be an abutment, as shown in FIGS. 1-3 and 5-6C, or the contact may be a coupling capable of transmitting one or more of tensile, compressive, torsional, and lateral forces. The contact may be selectively attachable and detachable in some embodiments by any effective mechanism. In some embodiments, the anchor system 100 may include a stay suture (not shown) that connects between the inserter 20 and the anchor 10. The stay suture may be tensioned to urge the anchor 10 toward the inserter 20 during insertion and then released when the inserter 20 is removed from the anchor 10. A stay suture may be removed from the anchor 10 by pulling one end of the stay suture entirely through the anchor 10, by severing the stay suture, or by any effective mechanism of removal. An extension shaft 21 is depicted in FIG. 3 proximal of and partially surrounding the outer shaft 22 and the rod 24. The inserter 20 illustrated also includes the rod 24 configured to fit within the outer shaft 22 and move within the outer shaft 22 (FIGS. 3 and 5-6C). The rod 24 is also configured to move within the anchor 10 when the outer shaft 22 is in position to push the anchor 10 into tissue. The rod 24 may be made from any functional material, but in some embodiments is made at least in part from a metal with a greater bending strength than the material from which the anchor is made. In other embodiments, a rod may be made from a material that is of the same or a lesser bending strength than an anchor. In such a case, the additional material of the rod may give the combined construct enough additional strength to meet design requirements that the anchor would not meet alone.

Figure 6C:
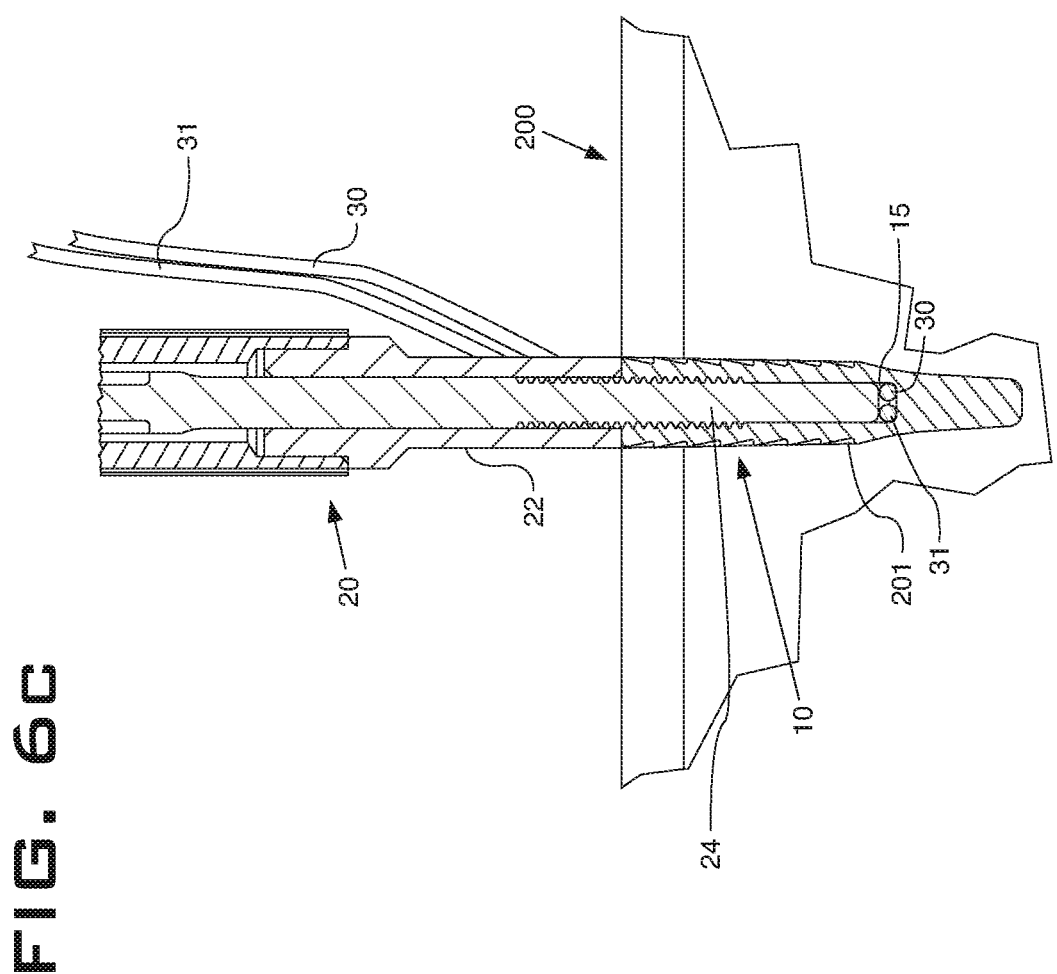
FIG. 6C is a cross-sectional view of the anchor, sutures, and distal end of the inserter of FIG. 1 having been implanted in tissue by pushing the anchor, sutures, and inserter into tissue.

Embodiments of the rod 24 are configured to go through the opening 11 in the proximal end 12 (FIG. 4) and to occlude the eyelet 13 when advanced distally within the anchor 10. The rod 24 is shown at various stages of advancement distally within the anchor 10 in FIGS. 5-6C. Specifically, the rod 24 is shown partially occluding the eyelet 13 in FIG. 6A. In FIGS. 5, 6B, and 6C, the rod 24 has been advanced further distally within the anchor 10 and is fully occluding the eyelet 13. The rod 24 and the anchor 10 are configured to removably couple to one another. In particular, the exterior of the rod 24 illustrated in FIG. 5 includes a thread 27 and the interior of the anchor 10 includes the thread 17, which matches the thread 27 such that rotating the rod 24 within the anchor 10 moves the rod 24 within the anchor and exercises a removable coupling between the rod 24 and the anchor 10. As used herein, the term "removably couple" or "removable coupling" means that the components are more positively and controllably attached together than components that merely abut or slide relative to one another. The illustrated embodiment depicts movement of the rod 24 relative to the anchor 10 by rotation of the rod 24. The rod 24 may be rotated by a knob or other mechanism that is a part of the inserter 20 and connects to the rod 24. Other embodiments may enable relative movement between a rod and an anchor or similar components by any effective mechanism, whether it be manual or powered by any operative source.

As shown in FIGS. 1-3 and 5-6C, the anchor system includes sutures 30, 31 configured to pass through the eyelet 13. In various embodiments, one or any number of sutures may be passed through an eyelet to achieve surgical objectives, as limited only by the sizes of the sutures and eyelet. The sutures 30, 31 are shown as two separate sutures, but in some embodiments may be a single suture doubled over and passed through an eyelet. A suture of the anchor system may be any suture, for example and without limitation, the suture may be a monofilament, multistrand, or woven construct. In some embodiments, the anchor system may be used to attach a tissue graft to another tissue element. For example and without limitation, the anchor system may be used to attach a ligament graft to a bone. In this example, the ligament graft or multiple grafts may be passed through an eyelet of an anchor, coupled with the assistance of a rod, and pushed into a bone in an essentially similar manner to the illustrated suture.

An embodiment of the invention is a method of anchoring tissue. The embodiment may include providing an anchor with an opening through its proximal end and an eyelet through the anchor that is transverse with and intersects the opening. For example, the anchor 10 with opening 11 and eyelet 13 may be used in conducting the method. The embodiment may also include providing an inserter that includes a rod configured to fit within the anchor. The inserter 20 with rod 24 and outer shaft 22 as described herein is an example of an inserter device that may be used. The method embodiment may include passing a suture, such as the sutures 30, 31 through the eyelet 13, as depicted in FIGS. 1-3. In this illustration, multiple sutures 30, 31 have been passed through the eyelet, but in other embodiments a single suture or one or more tissue grafts may be passed through the eyelet 13, or a similar eyelet. A suture may be passed through an anchor while the anchor is outside of a patient's body, or in some cases may be passed when the anchor is in whole or in part within a joint or other subcutaneous portion of a patient's body.

Method embodiments may further include advancing a rod, such as the rod 24, distally relative to the anchor 10. In particular in the example shown in FIGS. 5 and 6B, the rod 24 has been advanced distally through the opening 11 in the anchor 10 far enough to occlude the eyelet 13. In some embodiments, prior to the act of advancing the rod 24 distally through the opening 11 in the anchor 10 far enough to occlude the eyelet 13, the rod 24 is advanced toward a distal end of the eyelet 13, but not far enough to impinge on the suture. An example of this act is illustrated in FIG. 6A. In this state, the suture 30, 31 may remain free to move relative to the anchor 10 while the anchor is positioned in vivo. As shown in FIG. 6A, the anchor 10 has been place adjacent to tissue 200, which has a pre-drilled hole 201 into which the anchor may be pushed. The tissue 200 may be, for example and without limitation, a bone with an outer cortical layer covering a cancellous core. In the example anchoring system 100 shown in FIGS. 1-4 and 5-6C, the act of advancing the rod 24 distally through the opening 11 in the anchor 10 includes turning the rod 24 relative to the outer shaft 22 and the anchor 10, as described in more detail herein. As shown in FIGS. 5, 6B, and 6C, the rod 24 may also be advanced into the basin 15 formed in the anchor 10 distal of the eyelet 13. This act may secure the sutures 30, 31 relative to the anchor 10 by pinching the sutures between the eyelet 13 and the rod 24. This act may also or in the alternative increase the strength of the anchor system compared with the anchor 10 alone.

Another act of the method embodiment described here may include pushing an anchor, such as the anchor 10, into tissue, such as the tissue 200, at least as far as the proximal end 12 (FIG. 4) of the anchor 10 after the rod 24 has been advanced distally through the opening 11 in the anchor 10 far enough to occlude the eyelet 13. The result of this act is illustrated in FIG. 6C. The act of pushing the anchor 10 into the tissue 200 may also result in the suture being wedged between the anchor 10 and the tissue 200. As shown in FIGS. 6A-6C, method embodiments may also include the act of pre-drilling a hole 201 in the tissue 200 into which the anchor 10 may be pushed. In other embodiments, an anchor may be a push-in device that has a sharpened distal end or a tapping or drilling configuration that enables the anchor to be push into tissue without a hole being pre-drilled into the tissue. Such an anchor device may in some embodiments be made from metal or have a metal tip that may be sharpened or otherwise formed to promote its push-in functionality.

The rod 24, or a similar rod in other embodiments, may be removed proximally through the opening 11 in the anchor 10. In the illustrated embodiment, the rod 24 may be removed from the anchor 10 by rotating the rod 24 in a counterclockwise direction relative to the anchor 10 and then pulling the rod 24 and outer shaft 22 proximally away from the anchor 10. Once the anchor system 100 is in place as illustrated in FIG. 6C, the frictional resistance of the anchor 10 in the hole 201 in the embodiment shown is sufficient to allow the rod 24 to be rotated counterclockwise to move the rod 24 proximally away from the anchor 10, and subsequently to pull the rod 24 and outer shaft 22 away from the anchor 10. In other embodiments (not shown) a rotational constraint may be provided between an anchor and an inserter to positively lock movement between the anchor and the inserter while a rod is rotated or otherwise disengaged from the anchor. These acts will leave the anchor 10, along with the sutures 30, 31, implanted in the tissue 200. The sutures 30, 31 may then be carried forward to another anchor or to tissue to be surgically manipulated, may be cut, or may be knotted in some circumstances.

Another method embodiment is a method of securing a suture to a bone that also includes passing a suture through an eyelet in an anchor. The suture passing variations and example sutures, grafts, and anchor configurations are essentially similar to those describe in the method embodiment above. The method may also include engaging an inserter, such as the inserter 20, with an anchor, such as the anchor 10, and a suture to positively hold the suture relative to the anchor 10. The term "to positively hold" as used herein means to secure with a consistent force as applied by a clamp or threaded member and not merely to press on a suture with an unsecured and variable force as may be applied with an inserter held in a user's hand. As described with regard to the rod 24 and the anchor 10 herein, the act of engaging an inserter with the anchor 10 and the sutures 30, 31 to positively hold the sutures 30, 31 relative to the anchor 10 may include advancing a portion of the inserter 20, such as the rod 24, by turning the rod 24 relative to the outer shaft 22 and the anchor 10. The act of engaging an inserter with the anchor 10 may further include advancing a portion of the inserter 20, such as the rod 24, into the basin 15, as shown in FIGS. 5, 6B, and 6C, and as described in more detail in association with the method embodiment above. Descriptions and variations of this method are essentially similar to those describe with the method embodiment above with regard to wedging of the suture between an anchor and a bone, and with regard to acts associated with pre-drilling of holes into which an anchor may be pushed.

Method embodiments may include but are not limited to securing a suture to bone in performing a rotator cuff repair consistent with the acts described herein. In particular, the anchor system 100 may be used to secure a suture, such as the sutures 30, 31 to a humerus where one or both of the sutures 30, 31 have been attached to soft tissues of the rotator cuff. In the particular example of a double-row rotator cuff repair, an anchor 10 of the anchor system 100 may be used to secure one or more sutures to a humerus underneath soft tissues of the rotator cuff. The anchor 10 may also be used to secure one or more sutures into a humerus distal of the soft tissues of the rotator cuff. A common suture may be passed between and coupled to two or more anchors of such a construct or multiple sutures may be combined by tying or by coupling to two or more anchors.

Other method embodiments may include use of devices disclosed herein to perform a labral repair. For example and without limitation, one or more anchors 10 may be inserted into a glenoid bone. Sutures 30, 31 attached to the anchors may then be used to re-attach the labrum to the bone. A typical labral repair may require 1, 2, 3, or more anchors, depending on the location and size of the tear being repaired.

After the one or more anchors 10 are placed, the sutures 30, 31 may be run through the labrum and then pulled tight to re-attach the labrum to the glenoid. A common suture may be passed between and coupled to two or more anchors of such a construct or multiple sutures may be combined by tying or by coupling to two or more anchors.

Various embodiments of a system wholly or its components individually may be made from any biocompatible material. Instruments that will not be implanted and remain in a patient may not necessarily be biocompatible. For example and without limitation, materials may include in whole or in part: non-reinforced polymers, reinforced polymers, metals, ceramics, adhesives, reinforced adhesives, and combinations of these materials. Reinforcing of polymers may be accomplished with carbon, metal, or glass or any other effective material. Examples of biocompatible polymer materials include polyamide base resins, polyethylene, Ultra High Molecular Weight (UHMW) polyethylene, low density polyethylene, polymethylmethacrylate (PMMA), polyetheretherketone (PEEK), polyetherketoneketone (PEKK), a polymeric hydroxyethylmethacrylate (PHEMA), and polyurethane, any of which may be reinforced. Example biocompatible metals include stainless steel and other steel alloys, cobalt chrome alloys, zirconium, oxidized zirconium, tantalum, titanium, titanium alloys, titanium-nickel alloys such as Nitinol and other superelastic or shape-memory metal alloys. Sutures or other similar components of the invention may be single strand, woven, braided, or any combination thereof from any of these or other biocompatible materials. The sutures or other similar components may be any effective natural or synthetic material and may be a use or combination of materials well-known in the art. Sutures or other similar components of various embodiments may be resorbable or not resorbable.

Terms such as proximal, distal, far, underneath, and the like have been used relatively herein. However, such terms are not limited to specific coordinate orientations, distances, or sizes, but are used to describe relative positions referencing particular embodiments. Such terms are not generally limiting to the scope of the claims made herein. Any embodiment or feature of any section, portion, or any other component shown or particularly described in relation to various embodiments of similar sections, portions, or components herein may be interchangeably applied to any other similar embodiment or feature shown or described herein.

While embodiments of the invention have been illustrated and described in detail in the disclosure, the disclosure is to be considered as illustrative and not restrictive in character. All changes and modifications that come within the spirit of the invention are to be considered within the scope of the disclosure.

Embodiments of the invention may include claims to:

1. A method of anchoring to tissue comprising:
   providing an anchor with an opening through its proximal end and an eyelet through the anchor that is transverse with and intersects the opening;
   providing an inserter that includes a rod configured to thread into the opening in the anchor;
   passing a suture through the eyelet;
   advancing the rod distally through the opening in the anchor far enough to occlude the eyelet;
   pushing the anchor into tissue at least as far as the proximal end of the anchor after the rod has been advanced distally through the opening in the anchor far enough to occlude the eyelet; and
   removing the rod proximally through the opening in the anchor, leaving the anchor and the suture secured in the tissue.

2. The method of claim 1 wherein the act of passing a suture through the eyelet includes passing multiple sutures through the eyelet.

3. The method of claim 1 wherein prior to the act of advancing the rod distally through the opening in the anchor far enough to occlude the eyelet, the rod is advanced toward a distal end of the eyelet, but not far enough to impinge on the suture, such that the suture remains free to move relative to the anchor while the anchor is positioned in vivo.

4. The method of claim 1 wherein the act of advancing the rod distally through the opening in the anchor includes turning the rod relative to the anchor.

5. The method of claim 1 wherein the act of advancing the rod distally through the opening in the anchor includes advancing the rod into a basin formed in the anchor distal of the eyelet.

6. The method of claim 1 wherein the act of pushing the anchor into tissue results in the suture being wedged between the anchor and the tissue.

7. The method of claim 1, further comprising pre-drilling a hole into which the anchor is pushed.

8. A method of securing a suture to a bone comprising:
   passing a suture through an eyelet in an anchor;
   engaging an inserter with the anchor and the suture to positively hold the suture relative to the anchor by introducing a portion of the inserter into a cavity in the anchor, wherein the cavity in the anchor intersects with the eyelet, and the act of introducing the portion of the inserter causes the portion of the inserter to impinge on the suture within the cavity;
   pushing the anchor into the bone with the inserter such that the suture is wedged between the anchor and the bone, thereby substantially preventing movement of the suture relative to the anchor; and
   removing the inserter from the anchor, leaving the anchor and the suture secured in the bone.

9. The method of claim 8 wherein the act of passing a suture through an eyelet in an anchor includes passing multiple sutures through the eyelet.

10. The method of claim 8 wherein prior to introducing the portion of the inserter far enough into the anchor to impinge on the suture within the cavity, the portion of the inserter is inserted into the anchor toward a distal end of the eyelet, but not far enough to impinge on the suture, such that the suture remains free to move relative to the anchor while the anchor is positioned in vivo.

11. The method of claim 8 wherein the act of engaging an inserter with the anchor and the suture to positively hold the suture relative to the anchor includes turning a portion of the inserter inserted into the anchor relative to the anchor.

12. The method of claim 8 wherein the act of engaging an inserter with the anchor and the suture to positively hold the suture relative to the anchor includes advancing a portion of the inserter inserted into the anchor into a basin formed in the anchor distal of the eyelet.

13. The method of claim 8, further comprising pre-drilling a hole into which the anchor is pushed.

14. A method of securing a suture to a bone comprising:
   coupling the suture to an anchor system, the anchor system comprising:
      an anchor with an opening through its proximal end and an eyelet through the anchor that is transverse with and intersects the opening, and an inserter comprising an outer shaft configured to contact the anchor and to be used to push the anchor into tissue, and a rod housed within the outer shaft and the anchor, the rod extending through the opening in the proximal end of the anchor and configured to fully occlude the eyelet to impinge upon and secure the suture relative to the anchor when advanced distally within the anchor, pushing the anchor into the bone with the inserter such that the suture is wedged between the anchor and the bone, thereby substantially preventing movement of the suture relative to the anchor; and removing the inserter from the anchor, leaving the anchor and the suture secured in the bone.

15. The method of claim 14 wherein the act of coupling the suture to the anchor system includes coupling multiple sutures to the anchor system.

16. The method of claim 14 wherein prior to the rod being advanced distally through the opening in the anchor far enough to occlude the eyelet, the rod is advanced toward a distal end of the eyelet, but not far enough to impinge on the suture, such that the suture remains free to move relative to the anchor while the anchor is positioned in vivo.

17. The method of claim 14 wherein the rod is advanced distally through the opening in the anchor by turning the rod relative to the anchor.

18. The method of claim 14 wherein the rod is the only portion of the inserter housed within the anchor before the inserter is removed from the anchor.

19. The method of claim 14, further comprising pre-drilling a hole into which the anchor is pushed.

\* \* \* \* \*